United States Patent
Denis et al.

(10) Patent No.: US 11,078,173 B2
(45) Date of Patent: Aug. 3, 2021

(54) PROCESS FOR PRODUCING 5-HYDROXYMETHYLFURFURAL IN THE PRESENCE OF AN ORGANIC DEHYDRATION CATALYST AND A CHLORIDE SOURCE

(71) Applicant: IFP Energies nouvelles, Rueil-Malmaison (FR)

(72) Inventors: Justine Denis, Feyzin (FR); Marc Jacquin, Lyons (FR); Damien Delcroix, St Maurice L Exil (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 16/651,378

(22) PCT Filed: Sep. 25, 2018

(86) PCT No.: PCT/EP2018/075963
§ 371 (c)(1),
(2) Date: Mar. 27, 2020

(87) PCT Pub. No.: WO2019/063545
PCT Pub. Date: Apr. 4, 2019

(65) Prior Publication Data
US 2020/0290984 A1 Sep. 17, 2020

(30) Foreign Application Priority Data
Sep. 28, 2017 (FR) ...................................... 1759024

(51) Int. Cl.
| C07D 307/50 | (2006.01) |
| B01J 31/26 | (2006.01) |
| B01J 27/10 | (2006.01) |
| B01J 31/02 | (2006.01) |

(52) U.S. Cl.
CPC ............ *C07D 307/50* (2013.01); *B01J 27/10* (2013.01); *B01J 31/0225* (2013.01); *B01J 31/26* (2013.01); *B01J 2231/64* (2013.01)

(58) Field of Classification Search
CPC ..... C07D 301/50; B01J 31/0225; B01J 31/26; B01J 2231/64
See application file for complete search history.

(56) References Cited

U.S. PATENT DOCUMENTS

| 4,590,283 | A | 5/1986 | Gaset et al. |
| 9,617,235 | B2 | 4/2017 | Delcroix et al. |
| 10,421,735 | B2 | 9/2019 | Souleymanou et al. |
| 2010/0004437 | A1* | 1/2010 | Binder ................. C07D 307/28 536/124 |
| 2014/0235881 | A1 | 8/2014 | Cho et al. |
| 2014/0357878 | A1* | 12/2014 | Zhang .................. C07D 307/48 549/488 |
| 2015/0045576 | A1 | 2/2015 | Benecke et al. |
| 2015/0203461 | A1 | 7/2015 | Sabesan et al. |
| 2017/0233363 | A1* | 8/2017 | Bastioli ................ C07D 307/48 549/488 |

FOREIGN PATENT DOCUMENTS

| CH | 662353 | A5 | 9/1987 |
| WO | 13066776 | A1 | 5/2013 |
| WO | 15004369 | A1 | 1/2015 |
| WO | 17076626 | A1 | 5/2017 |

OTHER PUBLICATIONS

Chen Season S et al: "Valorization of cellulosic food waste into levulinic acid catalyzed by heterogeneous Brønsted acids: Temperature and solvent effects", Chemical Engineering Journal, Elsevier Sequoia, Lausanne, CH, vol. 327, Jun. 21, 2017 (Jun. 21, 2017), pp. 328-335, XP085186718, ISSN: 1385-8947, DOI: 10.1016/J.CEJ.2017.06.108.
International Search report PCT/2018EP/75963 dated Nov. 26, 2018 (pp. 1-22) and english language ISR (pp. 1-3).

* cited by examiner

Primary Examiner — Timothy R Rozof
(74) Attorney, Agent, or Firm — Millen White Zelano and Branigan, PC; John Sopp

(57) ABSTRACT

The invention relates to a novel process for converting a feedstock comprising at least one sugar into 5-hydroxymethylfurfural, wherein said feedstock is brought into contact with one or more organic dehydration catalysts and one or more chloride sources in the presence of at least one aprotic polar solvent alone or as a mixture, at a temperature of between 30° C. and 200° C., and at a pressure of between 0.1 MPa and 10 MPa.

12 Claims, No Drawings

PROCESS FOR PRODUCING 5-HYDROXYMETHYLFURFURAL IN THE PRESENCE OF AN ORGANIC DEHYDRATION CATALYST AND A CHLORIDE SOURCE

TECHNICAL FIELD OF THE INVENTION

The invention relates to a process for converting sugars and in particular hexoses into 5-hydroxymethylfurfural in the presence of organic dehydration catalysts and of a chloride source in the presence of at least one aprotic polar solvent.

PRIOR ART 5-hydroxymethylfurfural (5-HMF) is a compound derived from biomass which can be exploited in many fields, such as a precursor of active ingredients in pharmacy, agrochemistry or specialty chemistry. Its advantage in recent years has been its use as a precursor of furanedicarboxylic acid (FDCA) which is used as a substitute for terephthalic acid as a monomer for the production of polyester fibers or convenience plastics.

The production of 5-HMF by dehydration of hexoses has been known for many years and has been the subject of a large number of research works. On the one hand, the dehydration of glucose or fructose to 5-HMF is described in aprotic polar solvent, for example dimethyl sulfoxide DMSO or N-methylpyrrolidone NMP, in the presence of a heterogeneous acid catalyst, that is to say supported catalysts insoluble in the reaction medium, such as sulfonic silicas described by Bao et al., Catal. Common. 2008, 9, 1383, with performances corresponding to 5-HMF yields of approximately 70%. On the other hand, the dehydration of glucose or fructose to 5-HMF is described, for example in patent applications US 2014/0235881, US 2014/0357878 and US 2015/0045576, in aprotic polar solvent, for example water or ethanol, in the presence of heterogeneous or homogeneous acid catalysts, that is to say for the latter that they are soluble in the reaction medium, with the formation of by-products of the carboxylic acid, ester and ether family, such as levulinic acid and its esters, formic acid and its esters and also the alkoxylated derivatives of 5-HMF such as 5-ethoxymethylfurfural. The obtaining of these products imposes additional costly separation and purification steps detrimental to the economic profitability of the process.

There is therefore a need to develop new processes for the selective transformation of sugars into 5-HMF, making it possible to obtain better yields by limiting the formation of unwanted by-products.

Surprisingly, the applicant has demonstrated that bringing sugars into contact with one or more organic dehydration catalysts and one or more chloride sources in the presence of at least one aprotic polar solvent makes it possible to significantly increase the 5-HMF yields by limiting the formation of unwanted by-products, compared to these same dehydration catalysts used without a chloride source.

SUBJECT OF THE INVENTION

It is therefore an object of the present invention to provide a new process for converting a feedstock comprising at least one sugar into 5-hydroxymethylfurfural, wherein said feedstock is brought into contact with one or more organic acid catalysts and one or more chloride sources in the presence of at least one aprotic polar solvent alone or as a mixture, at a temperature of between 30° C. and 200° C., and at a pressure of between 0.1 MPa and 10 MPa.

One advantage of the present invention is to provide a process for converting sugars into 5-hydroxymethylfurfural (5-HMF) which makes it possible to increase the 5-HMF yield and to limit the formation of unwanted by-products such as the products of the carboxylic acid, ester, ether and humin family. Humins are secondary products of condensation resulting from the degradation of the sugars in an acid medium, such as polyfurans.

DEFINITIONS AND ABBREVIATIONS

It is specified, throughout this description, that the expression "of between . . . and . . . " should be understood as including the limits mentioned.

The term "organic acid dehydration catalyst" is intended to mean any catalyst chosen from organic Brønsted acids, which may be homogeneous or heterogeneous, capable of inducing dehydration reactions such as those of sugars to 5-hydroxymethylfurfural.

The term "chloride source" is intended to mean any compound capable of releasing a chloride ion (Cl⁻) of general formula $Q_yCl_z$ wherein Q can represent a hydrogen, an alkali or alkaline-earth metal chosen from groups 1 and 2 of the periodic table or an organic cation chosen from the ammonium, phosphonium and guanidinium family.

The term "homogeneous catalyst" is intended to mean a catalyst which is soluble in the reaction medium.

The term "heterogeneous catalyst" is intended to mean a catalyst which is insoluble in the reaction medium.

The term "organic catalyst" is intended to mean a catalyst wherein the acid function responsible for the catalytic dehydration activity is bonded to a hydrocarbon-based chain by a covalent bond.

The term "alkyl group" is intended to mean a linear or branched, and noncyclic, cyclic or polycyclic, saturated hydrocarbon-based chain containing between 1 and 20 carbon atoms.

The term "alkenyls" is intended to mean a hydrocarbon-chain containing between 1 and 20 atoms, comprising at least one, linear or branched, cyclic or non-cyclic unsaturation.

The term "aryl group" is intended to mean a mono or polycyclic, fused or non-fused aromatic group comprising between 5 and 30 carbons.

The term "heteroaryl group" is intended to mean an aromatic group comprising between 4 and 30 carbon atoms and at least, within at least one aromatic nucleus, one heteroatom chosen from oxygen, sulfur and nitrogen.

The term "alkyl halide group" is intended to mean an alkyl substituted with at least one halogen atom chosen from fluorine, chlorine, bromine or iodine.

The term "aprotic solvent" is intended to mean a molecule acting as a solvent and all the hydrogens of which are borne by carbon atoms.

The term "polar solvent" is intended to mean a molecule acting as a solvent, the dipole moment p of which, expressed in Debye, has a numerical value greater than or equal to 2.00 measured at 25° C.

The term "aprotic polar solvent" is therefore intended to mean a molecule acting as a solvent, all the hydrogens of which are borne by carbon atoms and the dipole moment p of which, expressed in Debye, has a numerical value greater than or equal to 2.00 measured at 25° C.

BRIEF DESCRIPTION OF THE INVENTION

Advantageously, the process according to the invention is a process for converting a feedstock comprising at least one sugar into 5-hydroxymethylfurfural, wherein said feedstock is brought into contact with at least one organic dehydration catalyst and at least one chloride source of general formula (III) $Q_yCl_z$ in the presence of at least one aprotic polar solvent, at a temperature of between 30° C. and 200° C. and a pressure of between 0.1 and 10 MPa, wherein Q is chosen from hydrogen, an alkali or alkaline-earth metal chosen from groups 1 and 2 of the periodic table or an organic cation chosen from the ammonium, phosphonium and guanidinium family.

y is between 1 and 10, z is between 1 and 10.

DETAILED DESCRIPTION OF THE INVENTION

Within the meaning of the present invention, the various embodiments presented can be used alone or in combination with one another, without any limit to the combinations.

The Feedstock

The feedstock treated in the process according to the invention is a feedstock comprising at least one sugar, preferably chosen from oligosaccharides and monosaccharides, alone or as a mixture.

The term "monosaccharide" denotes the compounds corresponding to the general formula (Ia) $C_6(H_2O)_6$ or $C_6H_{12}O_6$. Preferably, the monosaccharides are chosen from glucose, mannose and fructose, alone or as a mixture.

The term "oligosaccharide" denotes the compounds having the empirical formula (Ib) $C_{6n}H_{10n+2}O_{5n+1}$ wherein n is an integer between 1 and 10, the monosaccharide units making up said oligosaccharide being identical or different, and the compounds having the empirical formula (Ic) $(C_{6m}H_{10+2}O_{5m+1})(C_{5p}H_{8p+2}O_{4p+1})$ wherein m and p are independently integers between 1 and 10, the monosaccharide units making up said oligosaccharide being identical or different.

The oligosaccharides are preferably chosen from hexose oligomers or oligomers of pentoses and hexoses, preferably from hexose oligomers. They can be obtained by partial hydrolysis of polysaccharides from renewable resources such as starch, inulin, cellulose or hemicellulose, optionally from lignocellulosic biomass. Steam explosion of lignocellulosic biomass is a process of partial hydrolysis of the cellulose and hemicellulose contained in lignocellulosic biomass, producing a stream of oligo- and monosaccharides.

Preferably, the oligosaccharides are chosen from sucrose, lactose, maltose, isomaltose, inulobiose, melibiose, gentiobiose, trehalose, cellobiose, cellotriose, cellotetraose and oligosaccharides resulting from the hydrolysis of said polysaccharides resulting from the hydrolysis of starch, inulin, cellulose or hemicellulose, alone or as a mixture.

Preferably, the feedstock is chosen from cellobiose, fructose and glucose, alone or as a mixture. Very preferably, said feedstock is chosen from fructose and glucose, alone or as a mixture.

The Dehydration Catalysts

In accordance with the invention, said feedstock is brought into contact in the process with at least one organic dehydration catalyst chosen from homogeneous or heterogeneous organic Brønsted acids, capable of catalyzing the dehydration of the feedstock to 5-hydroxymethylfurfural.

Preferably, the homogeneous organic Brønsted acid catalysts are chosen from the organic acids of general formulae R'COOH, R'SO$_2$H, R'SO$_3$H, (R'O$_2$)NH, (R'O)$_2$PO$_2$H, R'OH, wherein R' is chosen from the:

alkyl groups, preferably comprising between 1 and 15 carbon atoms, preferably between 1 and 10, and preferably between 1 and 6, which are unsubstituted or substituted with at least one substituent chosen from a hydroxyl, an amine, a nitro, a halogen, preferably fluorine, and an alkyl halide, alkenyl groups which are unsubstituted or substituted with at least one group chosen from a hydroxyl, an amine, a nitro, an oxo, a halogen, preferably fluorine, and an alkyl halide, aryl groups, preferably comprising from 5 to 20 carbon atoms, preferably between 5 and 15 carbon atoms and preferably between 6 and 12 carbon atoms, which are unsubstituted or substituted with a substituent chosen from a hydroxyl, an amine, a nitro, an oxo, a halogen, preferably fluorine, and an alkyl halide, heteroaryl groups, preferably comprising between 4 and 15 carbon atoms and preferably between 4 and 12 carbon atoms, which are unsubstituted or substituted with a substituent chosen from a hydroxyl, an amine, a nitro, an oxo, a halogen, preferably fluorine, and an alkyl halide, When the catalysts of organic Brønsted acid type are chosen from the organic acids of general formulae R'—COOH, R' can also be a hydrogen.

Preferably, the organic Brønsted acids are chosen from formic acid, acetic acid, trifluoroacetic acid, lactic acid, levulinic acid, methanesulfinic acid, methanesulfonic acid, trifluoromethanesulfonic acid, bis(trifluoromethanesulfonyl)amine, benzoic acid, para-toluenesulfonic acid, 4-biphenylsulfonic acid, diphenyl phosphate, and 1,1'-binaphthyl-2,2'-diyl hydrogen phosphate. A very preferred homogeneous organic Brønsted acid catalyst is chosen from methanesulfonic acid (CH$_3$SO$_3$H) and trifluoromethanesulfonic acid (CF$_3$SO$_3$H).

The heterogeneous Brønsted acid catalysts are chosen from sulfonic acid resins (such as for example Amberlyst 15, 16, 35 or 36, Dowex 50 WX2, WX4 or WX8, Nafion PFSA NR-40 or NR-50, Aquivion PFSA PW 66, 87 or 98), carbons functionalized with sulfonic and/or carboxylic groups, and silicas functionalized with sulfonic and/or carboxylic groups. Preferably, the heterogeneous organic Brønsted acid catalyst is chosen from sulfonic acid resins.

The Chloride Sources

In accordance with the invention, in combination with the organic dehydration catalyst(s) defined above, said feedstock is brought into contact in the process according to the invention with one or more chloride sources of general formula (III) $Q_yCl_Z$ wherein Q is chosen from hydrogen, an alkali or alkaline-earth metal chosen from groups 1 and 2 of the periodic table or an organic cation chosen from the ammonium, phosphonium and guanidinium family.

y is between 1 and 10, preferably between 1 and 5 and preferably between 1 and 2;

z is between 1 and 10, preferably between 1 and 5 and preferably between 1 and 2.

Preferably, Q is a cation chosen from H, Li, Na, K, Rb, Cs, Fr, Mg, Ca, Sr and Ba, more preferably from H, Li, Na, K, Cs, Mg, Ca and Ba, and very preferably from H, Li, Na, K, Mg and Ca.

In the case where Q is an organic cation chosen from the ammonium family, the chloride source is chosen from the compounds corresponding to general formula (IIIa)

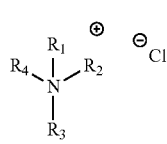

(IIIa)

wherein R₁ to R₄, which may be identical or different, are independently chosen from
- alkyl groups comprising from 1 to 20 carbons, optionally substituted with at least one group chosen from the following list: aldehyde —C(O)H, ketone —C(O)R", carboxylic acid —COOH, ester —COOR", hydroxymethyl —CH₂OH, ether —CH₂OR", halogenated —CH₂X with X=Cl, Br, I,
- aryl groups comprising from 5 to 20 carbons, optionally substituted with at least one group chosen from the following list: aldehyde —C(O)H, ketone —C(O)R", carboxylic acid —COOH, ester —COOR", hydroxymethyl —CH₂OH, ether —CH₂OR", halogenated —CH₂X with X=Cl, Br, I,
- wherein R" is an alkyl group comprising from 1 to 15 carbon atoms, preferably from 1 to 10 and preferably from 1 to 6.

Preferably, the groups R₁ to R₄, which may be identical or different, preferably linear, are independently chosen from alkyl groups preferably comprising between 1 and 15 carbon atoms, preferably between 1 and 10, preferably between 1 and 8, preferably between 1 and 6, and preferably from 1 to 4 carbon atoms.

Preferably, said groups R₁ to R₄ are chosen from alkyls substituted with at least one group chosen from —OH and —COOH.

Preferably, said groups R₁ to R₄ are independently chosen from n-butyl, methyl, n-octyl, hydroxymethyl, hydroxyethyl, hydroxypropyl, hydroxybutyl, —CH₂COOH, —CH₂CH₂COOH and CH₂CH₂CH₂COOH groups, preferably from the methyl, hydroxyethyl and —CH₂CH₂COOH groups.

Very preferably, the ammoniums are chosen from trioctylmethylammonium chloride ([CH₃(CH₂)₇)₃(CH₃)N⁺Cl⁻]), choline chloride ([(CH₃)₃NCH₂CH₂OH)⁺Cl⁻]), betaine chloride ([((CH₃)₃NCH₂COOH)³⁰ Cl⁻]), and tetramethylammonium chloride ([(CH₃)₄N⁺Cl⁻]).

In the case where Q is an organic cation chosen from the guanidinium chloride family, the chloride source is chosen from the compounds corresponding to general formula (IIIb)

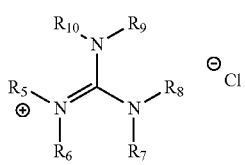

(IIIb)

wherein the groups R₅ to R₁₀, which may be identical or different, are independently chosen from hydrogen, and alkyl and aryl groups.

Preferably, the groups R₅ to R₁₀, which may be identical or different, are chosen from hydrogen, alkyl groups, which are preferably linear, comprising from 1 to 15 carbon atoms, preferably from 1 to 10 carbon atoms and preferably from 1 to 6 carbon atoms.

Preferably, the groups R₅ to R₁₀, which may be identical or different, are chosen from aryl groups comprising between 5 and 20 carbon atoms.

Very preferably, the groups R₅ to R₁₀, which may be identical or different, are independently chosen from hydrogen, and methyl, ethyl, propyl and butyl groups.

Preferably, in the case where Q is an organic cation chosen from the guanidinium family, the chloride source is guanidinium chloride and hexamethylguanidinium chloride.

In the case where Q is an organic cation chosen from the phosphonium family, the chloride source is chosen from the compounds corresponding to general formula (IIIc)

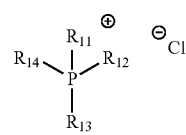

(IIIc)

wherein R₁₁ to R₁₄, which may be identical or different, are independently chosen from alkyl groups, aryl groups and phosphazene groups of general formula (IIId)

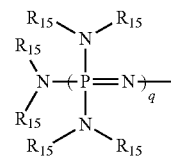

wherein R₁₅ is an alkyl group comprising from 1 to 10 carbon atoms, preferably from 1 to 5, and q is an integer between 0 and 10.

Preferably, R₁₁ to R₁₄, which may be identical or different, are chosen from alkyl groups, which are preferably linear, comprising from 1 to 15 carbon atoms, preferably between 1 and 10 carbon atoms and preferably from 1 to 6 carbon atoms.

Preferably, the groups R₁₁ to R₁₄, which may be identical or different, are chosen from
- a phosphazene group characterized by R₁₅=methyl and q=1,
- a methyl, ethyl, n-propyl, n-butyl group.

Preferably, in the case where Q is an organic cation chosen from the phosphonium family, the chloride source is tetraethylphosphonium chloride and tetra(n-butyl)phosphonium chloride.

Advantageously, the use of a chloride source in a conversion process in accordance with the invention makes it possible to limit the formation of unwanted by-products such as the products of the carboxylic acid, ester, ether and humin family.

Conversion Process

In accordance with the invention, the process for converting the feedstock comprising at least one sugar is carried out in a reaction chamber in the presence of at least one solvent, said solvent being an aprotic polar solvent or a mixture of aprotic polar solvents, at a temperature of between 30° C. and 200° C., and at a pressure between 0.1 MPa and 10 MPa.

The process is therefore carried out in a reaction chamber comprising at least one aprotic polar solvent and wherein said feedstock is placed in the presence of one or more dehydration catalysts and one or more chloride sources.

In accordance with the invention, the process is performed in the presence of at least one solvent, said solvent being an aprotic polar solvent or a mixture of aprotic polar solvents.

The aprotic polar solvents are advantageously chosen from all the aprotic polar solvents of which the dipole moment expressed in Debye (D) is greater than or equal to 2.00. Preferably, the aprotic polar solvents are chosen from pyridine (2.37), butan-2-one (5.22), acetone (2.86), acetic anhydride (2.82), N,N,N',N'-tetramethylurea (3.48), benzonitrile (4.05), acetonitrile (3.45), methyl ethyl ketone (2.76), propionitrile (3.57), hexamethylphosphoramide (5.55), nitrobenzene (4.02), nitromethane (3.57), N,N-dimethylformamide (3.87), N,N-dimethylacetamide (3.72), sulfolane (4.80), N-methylpyrrolidone (4.09), dimethyl sulfoxide (3.90), propylene carbonate (4.94) and γ-valerolactone (4.71) alone or as a mixture.

Preferably, the aprotic polar solvents are advantageously chosen from acetone, N,N-dimethylformamide, N,N-dimethylacetamide, sulfolane, N-methylpyrrolidone, dimethyl sulfoxide, propylene carbonate and γ-valerolactone alone or as mixture.

Preferably, the aprotic polar solvents are advantageously chosen from N,N-dimethylacetamide, N-methylpyrrolidone, dimethyl sulfoxide and γ-valerolactone alone or as a mixture. Very preferably, the solvent is dimethyl sulfoxide.

Preferably, said process according to the invention is performed at a temperature of between 40° C. and 175° C., preferably between 50 and 120° C., preferably between 60 and 100° C. and very preferably between 65 and 90° C., and at a pressure between 0.1 MPa and 8 MPa and preferably between 0.1 and 5 MPa.

Generally the process can be performed according to different embodiments. Thus, the process can advantageously be carried out batchwise or continuously. The process can be carried out in a closed reaction chamber or in a semi-open reactor.

The organic dehydration catalyst(s) are introduced into the reaction chamber in an amount corresponding to a feedstock/catalyst(s) weight ratio of between 1 and 1000, preferably between 1 and 500, preferably between 1 and 200, preferably between 1 and 150.

The chloride source(s) are introduced into the reaction chamber in an amount corresponding to a feedstock/chloride source(s) weight ratio of between 1 and 1000, preferably between 1 and 800, preferably between 1 and 500, preferably between 1 and 400.

The feedstock is introduced into the process in an amount corresponding to a solvent/feedstock weight ratio of between 0.1 and 200, preferably between 0.3 and 100 and more preferentially between 1 and 50.

If a continuous process is chosen, the weight hourly space velocity (flow rate of feedstock by weight/weight of catalyst(s)) is between 0.01 and 10 h$^{-1}$, preferably between 0.02 and 5 h$^{-1}$, preferably between 0.03 and 2 h$^{-1}$.

At the end of the reaction, the dehydration catalyst and the chloride source can be easily recovered by precipitation, distillation, extraction or washing.

The Products Obtained and the Method of Analysis Thereof

The product selectively obtained my means of the conversion process according to the invention is 5-hydroxymethylfurfural (5-HMF).

At the end of the reaction carried out in the process according to the invention, the reaction medium is analyzed by gas chromatography (GC) to determine the 5-HMF content in the presence of an internal standard, and by ion chromatography to determine the conversion of the feedstock in the presence of an external standard and to quantify the unwanted products such as levulinic acid and formic acid. The humins are quantified by difference in carbon balance with the carbon initially introduced.

EXAMPLES

The examples below illustrate the invention without limiting the scope thereof.

In the examples below, the glucose and fructose used as feedstock are commercially available and used without further purification.

The methanesulfonic acid denoted $CH_3SO_3H$ in the examples is commercially available and used without further purification.

The methanesulfonic acid denoted $CH_3SO_3H$, the lithium chloride denoted LiCl, the potassium chloride denoted KCl, the lithium bromide denoted LiBr, the lithium fluoride denoted LiF, the choline chloride denoted ChCl, the betaine chloride denoted BetC, and the tetramethylammonium chloride denoted TMACl, in the examples below are commercially available and used without additional purification.

The dimethyl sulfoxide, denoted DMSO in the examples, used as aprotic polar solvent, is commercially available and used without further purification.

For examples 1 to 8 of conversion of sugars into 5-HMF, the molar yield of 5-HMF is calculated by the ratio between the number of moles of 5-HMF obtained and the number of moles of sugar feedstock used.

Comparative Example 1: Fructose Conversion using Methanesulfonic Acid Alone in DMSO (Not in Accordance with the Invention)

The methanesulfonic acid (0.018 g, 0.19 mmol) is added to a solution of fructose (2.0 g, 11.10 mmol) in DMSO (20 g). The feedstock/catalyst weight ratio is 111. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 67%. The yield of unwanted humins is 26%.

Comparative Example 2: Fructose Conversion Using Lithium Chloride Alone in DMSO (not in Accordance with the Invention)

The lithium chloride (0.008 g, 0.19 mmol) is added to a solution of fructose (2.0 g, 11.10 mmol) in DMSO (20 g). The feedstock/catalyst weight ratio is 111. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography. The molar yield of 5-HMF after 6 h is 0%.

Example 3: Fructose Conversion Using Potassium Chloride Alone in DMSO (not in Accordance with the Invention)

The potassium chloride (0.014 g, 0.19 mmol) is added to a solution of fructose (2.0 g, 11.10 mmol) in DMSO (20 g).

The feedstock/catalyst weight ratio is 111. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 0%.

Example 4: Fructose Conversion using Methanesulfonic Acid and Lithium Chloride in DMSO (in Accordance with the Invention)

The methanesulfonic acid (0.018 g, 0.19 mmol) and the lithium chloride (0.008 g, 0.19 mmol) are added to a solution of fructose (2.0 g, 11.10 mmol) in DMSO (20 g). The feedstock/catalyst weight ratio is 111. The feedstock/chloride source weight ratio is 250. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 79%. The yield of unwanted humins is 12%.

Example 5: Fructose Conversion using Methanesulfonic Acid and Potassium Chloride in DMSO (in Accordance with the Invention)

The methanesulfonic acid (0.018 g, 0.19 mmol) and the potassium chloride (0.014 g, 0.19 mmol) are added to a solution of fructose (2.0 g, 11.10 mmol) in DMSO (20 g). The feedstock/catalyst weight ratio is 111. The feedstock/chloride source weight ratio is 140. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 75%. The yield of unwanted humins is 15%.

Example 6: Fructose Conversion using Methanesulfonic Acid and Choline Chloride in DMSO (in Accordance with the Invention)

The methanesulfonic acid (0.018 g, 0.19 mmol) and the choline chloride (0.027 g, 0.19 mmol) are added to a solution of fructose (2.0 g, 11.10 mmol) in DMSO (20 g). The feedstock/catalyst weight ratio is 111. The feedstock/chloride source weight ratio is 74. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 78%. The yield of unwanted humins is 12%.

Example 7: Fructose Conversion using Methanesulfonic Acid and Betaine Chloride in DMSO (in Accordance with the Invention)

The methanesulfonic acid (0.018 g, 0.19 mmol) and the choline chloride (0.029 g, 0.19 mmol) are added to a solution of fructose (2.0 g, 11.10 mmol) in DMSO (20 g). The feedstock/catalyst weight ratio is 111. The feedstock/chloride source weight ratio is 69. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 80%. The yield of unwanted humins is 10%.

Example 8: Fructose Conversion using Methanesulfonic Acid and Tetramethylammonium Chloride in DMSO (in Accordance with the Invention)

The methanesulfonic acid (0.018 g, 0.19 mmol) and the tetramethylammonium chloride (0.021 g, 0.19 mmol) are added to a solution of fructose (2.0 g, 11.10 mmol) in DMSO (20 g). The feedstock/catalyst weight ratio is 111. The feedstock/chloride source weight ratio is 95. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 80%. The yield of unwanted humins is 10%.

Comparative Example 9: Fructose Conversion using Methanesulfonic Acid and Lithium Bromide in DMSO (Not in Accordance with the Invention)

The methanesulfonic acid (0.018 g, 0.19 mmol) and the lithium chloride (0.016 g, 0.19 mmol) are added to a solution of fructose (2.0 g, 11.10 mmol) in DMSO (20 g). The feedstock/catalyst weight ratio is 111. The feedstock/bromide source weight ratio is 125. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 63%. The yield of unwanted humins is 32%.

Comparative Example 10: Fructose Conversion using Methanesulfonic Acid and Lithium Fluoride in DMSO (Not in Accordance with the Invention)

The methanesulfonic acid (0.018 g, 0.19 mmol) and the lithium fluoride (0.005 g, 0.19 mmol) are added to a solution of fructose (2.0 g, 11.10 mmol) in DMSO (20 g). The feedstock/catalyst weight ratio is 111. The feedstock/fluoride source weight ratio is 400. The solvent/feedstock weight ratio is 10. The reaction medium is then stirred at 70° C. at 0.1 MPa for 6 h. The conversion of fructose into 5-HMF is monitored by regularly taking samples of an aliquot of solution which is instantly cooled to 0° C., redissolved in water and checked by gas chromatography, and by ion chromatography. The molar yield of 5-HMF after 6 h is 0%.

TABLE 1

| Example | Feedstock | Dehydration catalyst | Chloride source | 5-HMF yield (%) | Unwanted products yield (%) |
|---|---|---|---|---|---|
| 1 (not in accordance with the invention) | Fructose | $CH_3SO_3H$ | — | 67 | Humins 26 |
| 2 (not in accordance with the invention) | Fructose | — | LiCl | 0 | — |
| 3 (not in accordance with the invention) | Fructose | — | KCl | 0 | — |
| 4 (in accordance with the invention) | Fructose | $CH_3SO_3H$ | LiCl | 79 | Humins 12 |
| 5 (in accordance with the invention) | Fructose | $CH_3SO_3H$ | KCl | 75 | Humins 15 |
| 6 (in accordance with the invention) | Fructose | $CH_3SO_3H$ | ChCl | 78 | Humins 12 |
| 7 (in accordance with the invention) | Fructose | $CH_3SO_3H$ | BetCl | 80 | Humins 10 |
| 8 (in accordance with the invention) | Fructose | $CH_3SO_3H$ | TMACl | 80 | Humins 10 |
| 9 (not in accordance with the invention) | Fructose | $CH_3SO_3H$ | LiBr | 63 | Humins 32 |
| 10 (not in accordance with the invention) | Fructose | $CH_3SO_3H$ | LiF | 0 | — |

The 5-HMF yield is higher in the case of the combination of a dehydration catalyst such as MSA and a chloride source such as LiCl, KCl, ChCl, BetCl or TMACl in an aprotic polar solvent according to the invention compared to the dehydration catalyst alone or the chloride source alone.

The yield of unwanted products such as humins is lower in the case of the association of a dehydration catalyst such as MSA and a chloride source such as LiCl, KCl, ChCl, BetCl or TMACl in an aprotic polar solvent according to the invention compared to the dehydration catalyst alone.

The 5-HMF yield is higher in the case of the combination of a dehydration catalyst such as MSA and a chloride source such as LiCl, KCl, ChCl, BetCl or TMACl in an aprotic polar solvent according to the invention compared to the combination of a dehydration catalyst in combination with a bromide source LiBr or a fluoride source LiF.

It therefore unexpectedly appears that it is clearly advantageous to use dehydration catalysts in combination with a chloride source in an aprotic polar solvent according to the invention for the conversion of sugars into 5-HMF.

The invention claimed is:

1. A process for converting a feedstock comprising at least one sugar into 5-hydroxymethylfurfural, which comprises bringing said feedstock into contact with at least one organic dehydration catalyst independently chosen from homogeneous and heterogeneous organic Brønsted acids, and at least one chloride source in the presence of at least one aprotic polar solvent, at a temperature of between 30° C. and 200° C. and a pressure of between 0.1 and 10 MPa,
wherein the chloride source is:
an organic cation of the guanidium family chosen from compounds of formula (IIIb)

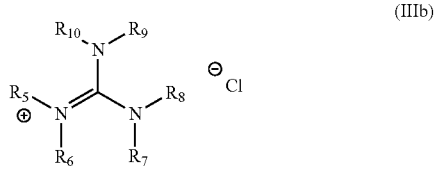
(IIIb)

wherein the groups $R_5$ to $R_{10}$, which may be identical or different, are independently chosen from alkyl groups comprising between 1 and 20 carbon atoms, and aryl groups comprising between 5 and 20 carbon atoms, or
an organic cation of the phosphonium family chosen from compounds of formula (IIIc)

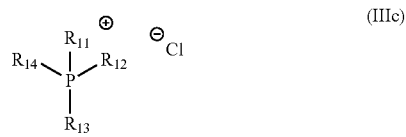
(IIIc)

wherein $R_{11}$ to $R_{14}$, which may be identical or different, are independently chosen from
- alkyl groups, comprising between 1 and 20 carbon atoms,
- aryl groups, comprising between 5 and 20 carbon atoms, and
- phosphazene groups of general formula

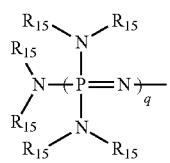

wherein $R_{15}$ is an alkyl group comprising from 1 to 10 carbon atoms, and q is an integer between 0 and 10.

2. The process as claimed in claim 1, wherein the feedstock is chosen from oligosaccharides and monosaccharides, alone or as a mixture.

3. The process as claimed in claim 1, wherein the feedstock is chosen from sucrose, lactose, maltose, isomaltose, inulobiose, melibiose, gentiobiose, trehalose, cellobiose, cellotriose, cellotetraose and oligosaccharides resulting from the hydrolysis of said polysaccharides resulting from the hydrolysis of starch, inulin, cellulose or hemicellulose, alone or as a mixture.

4. The process as claimed in claim 1, wherein the dehydration catalyst is an organic Brønsted acid chosen from the organic acids of general formulae R'COOH, R'SO$_2$H, R'SO$_3$H, (R'SO$_2$)NH, (R'O)$_2$PO$_2$H, R'OH, wherein R' is chosen from
- alkyl and alkanol groups comprising from 1 to 20 carbon atoms,
- aryl and heteroaryl groups preferably comprising between 4 and 20 carbon atoms, and
- a hydrogen when the acid chosen corresponds to general formula R'COOH.

5. Process as claimed in claim 1, wherein the dehydration catalyst is a heterogeneous organic Brønsted acid chosen from sulfonic acid resins, carbons functionalized with sulfonic and/or carboxylic groups, and silicas functionalized with sulfonic and/or carboxylic groups.

6. The process as claimed in claim 1, wherein the chloride source is an organic cation of the guanidium family chosen from compounds of formula (IIIb).

7. The process as claimed in claim 1, wherein the chloride source is an organic cation of the phosphonium family chosen from compounds of formula (IIIc).

8. The process as claimed in claim 1, wherein the aprotic polar solvent(s) are chosen from all the aprotic polar solvents of which the dipole moment expressed in Debye (D) is greater than or equal to 2.00.

9. The process as claimed in claim 1, wherein at least one aprotic polar solvent, alone or as a mixture, is chosen from pyridine, butan-2-one, acetone, acetic anhydride, N,N,N',N'-tetramethylurea, benzonitrile, acetonitrile, methyl ethyl ketone, propionitrile, hexamethylphosphoramide, nitrobenzene, nitromethane, N,N-dimethylformamide, N,N-dimethylacetamide, sulfolane, N-methylpyrrolidone, dimethyl sulfoxide, propylene carbonate and γ-valerolactone.

10. The process as claimed in claim 1, wherein the feedstock is introduced into the process in a weight ratio of the solvent to the feedstock (solvent/feedstock) of between 0.1 and 200.

11. The process as claimed in claim 1, wherein the organic dehydration catalyst(s) are introduced into the reaction chamber in a weight ratio of the feedstock to the catalyst (feedstock/catalyst) of between 1 and 1000.

12. The process as claimed in claim 1, wherein the chloride source(s) are introduced into the reaction chamber in a weight ratio of the feedstock to the chloride source(s) (feedstock/chloride source(s)) of between 1 and 1000.

* * * * *